United States Patent [19]

Mark

[11] 4,358,613

[45] Nov. 9, 1982

[54] PROCESS FOR THE PREPARATION OF SUBSTITUTED GUANIDINES

[75] Inventor: Victor Mark, Evansville, Ind.

[73] Assignee: General Electric Company, Mt. Vernon, Ind.

[21] Appl. No.: 243,732

[22] Filed: Mar. 16, 1981

Related U.S. Application Data

[63] Continuation of Ser. No. 107,057, Dec. 26, 1979, abandoned.

[51] Int. Cl.$^3$ ........................................... C07C 129/12
[52] U.S. Cl. ................................. 564/238; 564/230; 564/237; 564/240
[58] Field of Search ............... 564/238, 237, 230, 231, 564/240

[56] References Cited

PUBLICATIONS

Bredereck, Hellmut et al., *Chem. Ber.*, vol. 94, pp. 2278–2295, (1961).
Eilingsfeld, Heinz et al., *Chem. Ber.*, vol. 97, pp. 1232–1245, (1964).
Gavin, David F. et al., *J. Org. Chem.*, vol. 32, pp. 2511–2516, (1967).
Smith, P. A. S., *Open-chain Nitrogen Compounds*, vol. 1, pp. 281–282, (1965).

*Primary Examiner*—Natalie Trousof
*Assistant Examiner*—L. Hendriksen
*Attorney, Agent, or Firm*—Martin B. Barancik; William F. Mufatti

[57] ABSTRACT

Guanidines are one of the strongest organic bases and find applications where this property is needed, such as in phase transfer catalysis in the form of their substituted derivatives. Their use, however, has been hampered by their expensive nature due to the only mediocre yields in their preparation. The present invention provides a process for the preparation of substituted guanidines in high yields.

6 Claims, No Drawings

PROCESS FOR THE PREPARATION OF SUBSTITUTED GUANIDINES

This is a continuation, of copending application Ser. No. 107,057, filed 12/26/79, now abandoned.

BACKGROUND OF THE INVENTION

The most general and widely used method for obtaining substituted guanidines (B) is from corresponding substituted (aminomethylene) ammonium halides (A) with one mole of a primary amine:

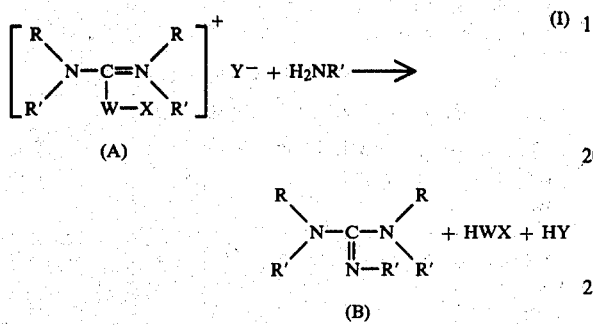

wherein X is a monovalent substituent selected from the following radicals: $-P(O)Cl_2$; $-PCl_4$; $-S(O)Cl$; $-S(O)-R$ and $-C(O)-R'$; W is oxygen or sulfur; Y is chlorine or bromine; R is a monovalent substituent selected from the group consisting of hydrogen, alkyl, aryl, aralkyl, alkaryl, cycloalkyl, alkenyl, cycloalkenyl and heterocyclic radical; R' is a monovalent organic radical independently selected from the group consisting of alkyl, aryl, aralkyl, alkaryl, cycloalkyl, alkenyl, cycloalkenyl and heterocyclic radical.

The yields are, however, only mediocre and vary in general from 40 to 70% of the theory, as documented in (a) *Journal of Organic Chemistry*, Vol. 32, pp. 2511-2516 (1967); (b) *Chemische Berichte*, Vol. 94, pp. 2278-2295 (1961); and in the book (c) of P. A. S. Smith, *Open-chain Nitrogen Compounds*, Vol. 1, pp. 281-282, (1965), W. A. Benjamin, Inc. New York.

Compounds of general formula (A) are available by the reaction of substituted ureas with one of the following reactants: $P(O)Cl_3$, $PCl_5$, $SOCl_2$, $RS(O)Cl$ and $RC(O)Y$:

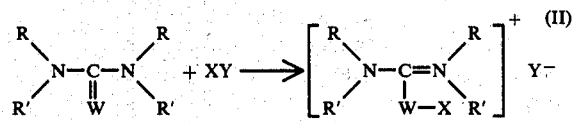

wherein X,Y,W,R and R' are as defined above. In contrast to reaction (I), the yields in reaction II are generally high, varying from 80 to 99%, as indicated in reference (b) quoted above.

SUMMARY OF THE INVENTION

It has now been found that reaction I can be made very facile and essentially quantitative by adding together with the primary amine one of the following coreactants:

(a) at least one, but preferably two, moles of a tertiary amine of high basicity;

(b) at least one, but preferably two, moles of a strong inorganic base;

(c) at least one, but preferably two, additional moles of the primary amine reactant;

(d) at least one, but preferably two, moles of the guanidine product formed in the reaction.

The role of the strong base in reaction I is not only to liberate the amine reactant that is partially inactivated by being tied up as its hydrohalide, but to participate actively in the reaction, which is shown in its simplified form by equation I. Actually, there are two reaction intermediates (C) and (D) leading from (A) to (B):

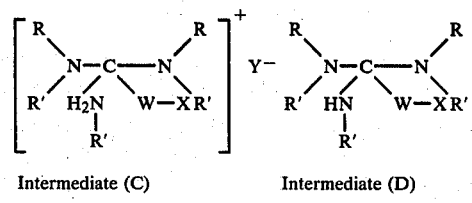

Intermediate (C)    Intermediate (D)

wherein R, R', W, X and Y are as above. The added organic or inorganic base facilitates the conversion of (C) to (D) and then to (B), thus not only increasing the yield but the reaction rate as well.

Examples of strong inorganic bases which can be employed are alkali or alkaline earth metal hydroxides, such as sodium hydroxide, potassium hydroxide and calcium hydroxide.

Strong organic bases which can be employed are represented by tertiary aliphatic and cycloaliphatic amines, dialkyl anilines, di- or poly(tertiary) amines, and the like, and include such compounds as triethyl amine, tripropyl amine, tributyl amine, dicyclohexylmethyl amine, diisopropylaniline, quinuclidine and hexamethylenetetramine.

In one preferred embodiment, the extra organic base is the primary amine ($H_2NR'$) of equation (I). Examples of such primary amines include methylamine, ethylamine, propylamine, isopropylamine, tert-butylamine, octadecylamine, aniline, p-chloroaniline, 4-aminopyridine, ethanolamine, 2-methoxyethylamine and similar substituted aliphatic, cycloaliphatic, aromatic and heterocyclic amines.

In another preferred embodiment, the extra organic base is the guanidine itself, that is the reaction product of equation (I). This is a particularly preferred variation in that guanidines are more powerful bases than any of the tertiary amines, or the primary amines required in equation (I), and are thus capable to effect quantitative conversions. Furthermore, the reactions are especially clean, since there are no extraneous products formed and, thus, there is no need of extra separation steps, such as distillation. The guanidine hydrochloride tied up in the reaction can be set free by concentrated aqueous sodium hydroxide solution and then be reused anew.

The preparation of guanidines is best carried out without the isolation of (A), which is moisture sensitive. Instead, reactions (II) and (I) are combined and carried out in the same reactor, with complete exclusion of moisture, to secure maximum, often quantitative yields. It is, therefore, best to introduce reagent XY into a solution or slurry of the urea or thiourea in an inert liquid until the reaction is complete, as evidenced by the cessation of the exotherm. The primary amine is then introduced, in excess or in the presence of the tertiary amine or guanidine. The reaction is facile and usually exothermic. Internal (such as by the refluxing solvent) or external cooling is applied to maintain the reaction temperature at optimum levels, which is between 0° and 100° C., preferably 30° and 50° C. When inorganic bases are used, they are best introduced after the theoretical amount of primary amine has been added. Preferably, the addition of the inorganic base is gradual, so as to minimize the hydrolysis of A to the urea. It is also best to use relatively concentrated (40–50%) solutions of sodium or potassium hydroxide or slurries of calcium hydroxide or barium hydroxide. If the guanidine formed is liquid, it is best separated from the aqueous brine by phase separation. If solid, the guanidine is best filtered off, washed and dried.

EXAMPLE 1

N,N,N',N'-Tetramethyl-N''-phenylguanidine

This Example illustrates conventional methods, such as disclosed in references (a) and (b), for the preparation of the title guanidine, in which only a mediocre yield is attained.

A solution of 58.1 g (0.5 mole) of dry tetramethylurea in 250 ml of benzene was charged to a one liter, four necked flask equipped with a mechanical stirrer, a thermometer reaching into the liquid, a reflux condenser and an addition funnel. A solution of 76.5 g of phosphorus oxychloride in 50 ml of benzene was added dropwise, in the course of 1.5 hrs., while stirring and maintaining the temperature of the ensuing exothermic reaction below 25° C. After standing overnight at ambient temperature, a solution of 46.5 g of aniline in 50 ml of benzene was added at ambient temperature, followed by an 8 hr. heating period at 75° C. After cooling to ambient temperature stirring was stopped, whereupon the reaction mixture was separated into two immiscible layers. The lower layer was washed twice with 100 ml of benzene and the washings combined with the upper layer, washed with dilute sodium hydroxide solution and water, separated, dried and the solvent removed on a rotary evaporator at water aspirator vacuum. Fractional distillation of the oily residue yielded, after a cut consisting of recovered aniline, a colorless oil, boiling at 80°–82° C. at 0.1 mm mercury vacuum, having a refractive index of $n_D^{20}$ 1.5696, identified by ir and proton mmr as well as elemental analysis as N,N,N',N'-tetramethyl-N''-phenylguanidine (TMPG). The yield was only 50 grams or 52% of the theoretical amount.

EXAMPLE 2

This Example illustrates the preparation of TMPG following the process of the invention wherein an excess of aniline was employed.

The procedure of Example 1 was repeated, except that the overnight aging and the heating at 75° C. for 8 hrs. were omitted, and the amount of aniline added was doubled (to 93.1 g). The yield was 95.0 grams or 78% of theory.

EXAMPLE 3

This example illustrates another embodiment of the invention wherein TMPG was prepared in the presence of a strong inorganic base.

The procedure of Example 2 was exactly repeated, except that, after the addition of only 46.5 g of aniline, there was slowly added 45 g (1.1 mole) of sodium hydroxide in form of a 50% aqueous solution. Subsequent workup by water treatment and distillation (as disclosed in Example 1), yielded 80.2 g of TMPG, which corresponds to an 85% yield.

EXAMPLE 4

This example illustrates a further embodiment of the invention wherein TMPG was prepared in the presence of TMPG.

The procedure of Example 2 was exactly repeated, except that a solution of 46.6 g (0.5 mole) of aniline in 96.0 g (0.5 mole) of TMPG was substituted for the benzene solution of aniline. The distilled product, which included the TMPG added in the reaction weighed 190 g. and was found by gas chromatography to be 98.5% pure. The yield of the TMPG produced in the reaction was, accordingly, 98%.

EXAMPLE 5

N''-Butyl-N,N,N',N'-Tetramethylguanidine

This example illustrates the preparation of the titled guanidine in the presence of a strong organic base following another embodiment of the invention.

The procedure of Example 4 was repeated, except that the solution of aniline in TMPG was replaced with a solution of n-butylamine (36.6 g, 0.5 mole) in triethylamine (51 g, 0.5 mole). Workup and distillation, as indicated, yielded 72.0 g (0.42 mole) of N''-butyl-N,N,N',N'-tetramethyl guanidine, bp. 31°–32° C. at 0.03 mm, $n_D^{22.3}$ 1.4600, which corresponded to 84% yield of the theory.

EXAMPLE 6

The procedure of Example 4 was repeated except that 60 g of thionyl chloride was substituted for the 76.5 g of phosphorus oxychloride. Workup and distillation yielded 90% of TMPG.

What I claim is:

1. In a process for preparing a guanidine which comprises reacting a substituted (aminomethylene) ammonium halide and a primary amine, the improvement consisting of carrying out the reaction in the presence of at least equimolar amounts of a coreactant strong base selected from the group consisting of
   A. tertiary amines;
   B alkali or alkaline earth metal hydroxides;
   C the guanidine itself that is the product of the reaction;
   D the primary amine reactant itself wherein the primary amine, R'NH$_2$, is used in at least one molar excess above the stoichiometric amount;
   E quaternary ammonium hydroxides.

2. The process of claim 1 wherein the substituted (aminomethylene)ammonium halide is represented by the following formula

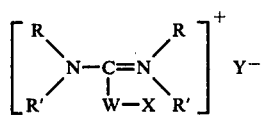

wherein X is a monovalent substituent selected from the following radicals: —P(O)Cl$_2$; —PCl$_4$; —S(O)Cl; —S(O)—R and —C(O)—R'; W is oxygen or sulfur; Y is chlorine or bromine; R is a monovalent substituent selected from the group consisting of hydrogen, alkyl, aryl, aralkyl, alkaryl, cycloalkyl, alkenyl and cycloalkenyl; R' is a monovalent organic radical independently selected from the group consisting of alkyl, aryl, aralkyl, alkaryl, cycloalkyl, alkenyl and cycloalkenyl.

3. The process of claim 8 wherein the primary amine is represented by the following formula:

R'—NH$_2$ wherein R' is alkyl, aryl, aralkyl, alkaryl, cycloalkyl, alkenyl or cycloalkenyl.

4. The process of claim 1 wherein the tertiary amine is selected from the group consisting of trialkyl amine, cycloalkyl dialkylamine, dicycloalkyl-alkylamine, tricycloalkylamine, triaralkylamine, dialkyl arylamine, dicycloalkylarylamine and pyridines.

5. The process of claim 1 wherein the alkali or alkaline metal hydroxide is selected from the group consisting of sodium hydroxide, potassium hydroxide and calcium hydroxide.

6. The process of claim 1 wherein the quaternary ammonium hydroxide is represented by the formula

[R$_4$N]$^+$HO$^-$ wherein R is hydrogen, alkyl, aryl, aralkyl, alkaryl, cycloalkyl, alkenyl or cycloalkenyl.

* * * * *